United States Patent [19]
Yamada et al.

[11] Patent Number: 5,759,365
[45] Date of Patent: Jun. 2, 1998

[54] OXYGEN CONCENTRATION SENSOR

[75] Inventors: Hirokazu Yamada; Takashi Kojima. both of Kariya, Japan

[73] Assignee: Nippondenso Co. Ltd., Kariya, Japan

[21] Appl. No.: 609,421

[22] Filed: Mar. 1, 1996

[30] Foreign Application Priority Data

Mar. 3, 1995 [JP] Japan .................... 7-070760

[51] Int. Cl.$^6$ .................................. G01N 27/409
[52] U.S. Cl. ................ 204/424; 204/408; 204/421; 204/427; 204/428
[58] Field of Search ................ 204/421–429, 204/408; 248/314, 316.1, 316.7; 267/158, 159, 164, 182

[56] References Cited

U.S. PATENT DOCUMENTS

| | | | |
|---|---|---|---|
| 2,100,042 | 11/1937 | Travis | 248/314 |
| 3,835,012 | 9/1974 | Hemak | 204/428 |
| 4,540,070 | 9/1985 | Yonovich et al. | 267/141 |
| 4,556,475 | 12/1985 | Bayha et al. | 204/427 |
| 4,741,816 | 5/1988 | Nishio et al. | 204/425 |
| 4,824,550 | 4/1989 | Ker et al. | 204/427 |
| 5,098,548 | 3/1992 | Duce | 204/427 |

FOREIGN PATENT DOCUMENTS

| | | |
|---|---|---|
| 61-027010 | 2/1986 | Japan . |
| 5-006529 | 2/1993 | Japan . |
| 6-003430 | 1/1994 | Japan . |

*Primary Examiner*—T. Tung
*Attorney, Agent, or Firm*—Cushman Darby & Cushman IP Group of Pillsbury Madison & Sutro LLP

[57] ABSTRACT

According to the present invention, an oxygen concentration sensor for detecting an oxygen concentration includes a sensor element having an atmospheric chamber therein, a heater inserted in the atmospheric chamber, and a holder for holding the heater in the atmospheric chamber. The holder includes a cylindrical portion for covering an outer periphery of the heater, and a plurality of cantilever elastic pieces provided at a lower portion of the cylindrical portion. The elastic pieces includes a heater supporting portion elastically contacting with the periphery of the heater and a fixing portion elastically contacting with an inner surface of the sensor element. In this way, it is possible to assemble a heater into a sensor element easily without causing damage to the heater.

12 Claims, 14 Drawing Sheets

OXYGEN CONCENTRATION SENSOR

CROSS REFERENCE TO RELATED APPLICATION

This application is based on and claims priority of from Japanese Patent Application No. 7-70760 filed on Mar. 3, 1995 incorporated herein by reference.

BACKGROUND OF THE INVENTION

1. Field of the Invention

The present invention relates to an oxygen concentration sensor used for air/fuel ratio control of an automobile engine.

2. Description of Related Art

As for an oxygen concentration sensor including a sensor element having an atmospheric chamber therein and a heater inserted into the atmospheric chamber with a holder, a conventional oxygen concentration sensor described as follows has been known (Japanese Examined Application No. Hei 6-3430).

Figure 14:
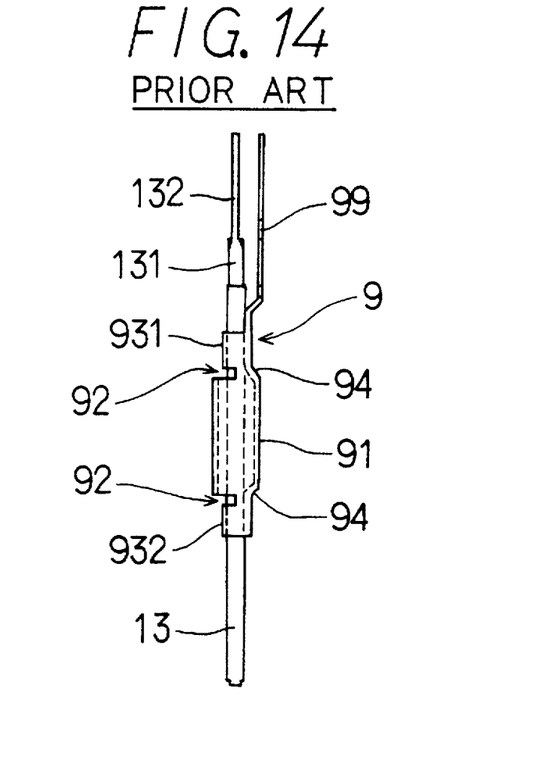
FIG. 14 is an explanatory view illustrating the assembly of a holder and a heater according to prior arts.

As shown in FIG. 14, the above-mentioned holder 9 is in a substantially tubular shape and has an electrode contacting portion 91 electrically conducted to an inner electrode which is disposed inside of the atmospheric chamber.

Holding portions 931 and 932 are provided at an upper end and a lower end of electrode connecting portion 91, respectively with slotted portions 92 therebetween. A heater 13 is fixedly inserted into holding portions 931 and 932.

In addition, a lead portion 99 for taking an output out of the inner electrode to the outside extends from holding portion 931.

Figure 15:
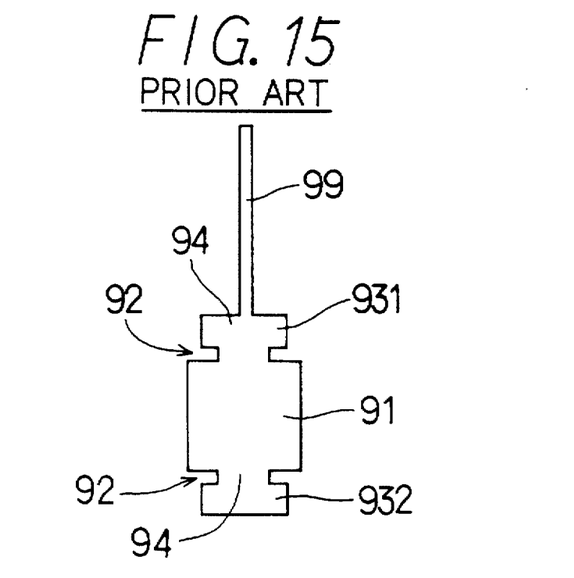
FIG. 15 is a plan development view illustrating the holder according to the prior arts.

Accordingly, holder 9 is formed of a metal plate which is punched in a predetermined configuration as shown in FIG. 15.

The metal plate is bent at its middle portion to form the tubular electrode connecting portion 91 having a diameter larger than that of the sensor element. Then, heater 13 is inserted into the bent metal plate, i.e., holder 9, in order to fix heater 13 to holding portions 931 and 932.

At this time, curved portions 94 are formed between electrode connecting portion 91 and holding portions 931 and 932 in such a manner that a central axis of electrode connecting portion 91 and a central axis of holding portions 931 and 932 are arranged in a same straight line.

When heater 13 is assembled into the sensor element, the heater is inserted in the atmospheric chamber while reducing a diameter of electrode connecting portion 91 of holder 9. Then, elastic force is applied to electrode connecting portion 91 and presses the inner electrode in the atmospheric chamber radially. As a result, heater 13 is fixedly supported in the atmospheric chamber.

In addition, since electrode connecting portion 91 contacts with the inner electrode by the elastic force, the output of the inner electrode can be taken out via lead portion 99 provided on holder 9.

However, when heater 13 is fixed with the above-mentioned holder 9, the elastic force is radially applied toward electrode connecting portion 91 which is a tubular-shaped spring. Because the elastic force varies greatly even when a displacement amount of electrode connecting portion 91 slightly fluctuates, a tolerance in manufacturing the holder is restricted, thus making it difficult to manufacture a holder.

In addition, as the above-mentioned electrode connecting portion 91 having a diameter larger than that of the atmospheric chamber in the sensor element, connecting portion 91 should be assembled into the atmospheric chamber while reducing its diameter. Therefore, it is difficult to assemble holder 9 into the sensor element, thus taking a long time.

Furthermore, since heater 13 in holder 9 is fixedly supported at two vertical holding portions 931 and 932, heater 13 may be damaged when the oxygen concentration sensor externally is shocked.

SUMMARY OF THE INVENTION

In light of the above-described problem, the present invention provides an oxygen concentration sensor capable of assembling a heater into a sensor element easily without causing damage to the heater.

According to the present invention, an oxygen concentration sensor for detecting an oxygen concentration includes a sensor element having an atmospheric chamber therein, a heater inserted in the atmospheric chamber, and a holder for holding the heater in the atmospheric chamber. The holder includes a cylindrical portion for covering an outer periphery of the heater, and a plurality of cantilever elastic pieces provided at a lower portion of the cylindrical portion. The elastic pieces includes a heater supporting portion elastically contacting with the periphery of the heater and a fixing portion elastically contacting with an inner surface of the sensor element. In this way, it is possible to assemble a heater into a sensor element easily without causing damage to the heater.

The cantilever elastic pieces may be a plate-shaped portion extending downwardly from the cylindrical portion. As an upper end portion of the cantilever elastic pieces is a fixed end, while a lower end portion is a free end.

The heater supporting portion and the fixing portion may be formed by bending the cantilever elastic pieces radially toward the inside or outside of the cylindrical portion properly. It may be possible for a plurality of bending portions to be provided at one cantilever elastic piece. An inner electrode may be formed on the inner surface of the sensor element where the fixing portion of the elastic piece contacts. In such a case, the fixing portion functions as the electrode connecting portion.

When the heater supporting portion and the electrode connecting portion are provided to the cantilever elastic pieces, the following structure can be considered.

First, the heater supporting member and the electrode connecting portion can be provided at middle portion and lower end portion of the cantilever elastic pieces, respectively. Conversely, the electrode supporting member can be provided at the middle of the cantilever elastic pieces with the heater supporting portion at the lower end portion.

The heater supporting portion may be provided at the middle of one cantilever elastic piece with the electrode connecting portion at the lower end portion thereof, while the electrode connecting portion may be provided at the middle of another cantilever elastic piece with the heater supporting member at the middle portion thereof.

Furthermore, one cantilever elastic piece may include only the heater supporting portion while another cantilever elastic piece includes only the electrode connecting portion. It is preferable that this case is applied to a holder having four or more of cantilever elastic piece so that the heater can be supported in good balance.

Next, it is preferable that the cylindrical portion in the above-mentioned holder includes a flange portion at an upper portion of the cylindrical portion. The flange is engaged with the upper portion of the sensor element, thereby preventing the holder from falling into the atmospheric chamber.

The holder preferably includes a lead portion for taking out the output of the inner electrode. For this reason, the holder can function as a lead wire for taking out the output of the inner electrode, thereby reducing the number of component parts.

In addition, it is preferable that the cylindrical portion is integrally formed with the cantilever elastic pieces. For this reason, the holder can be manufactured by simple process and method such as a method for producing a holder by punching a metal plate into a desired configuration and bending such metal plate.

When the heater is assembled into the sensor element, the holder may be inserted into the sensor element, and sequentially the heater may be inserted in the holder.

In this case, it is preferable that the maximum diameter of the arc formed between each of tip portions of the elastic pieces at the holder is smaller than a diameter of the atmospheric chamber, for example.

Accordingly, the heater can be assembled with simple without damaging the inner electrode inside of the sensor element.

Furthermore, the heater may be inserted in the holder in advance, and then the holder with the heater may be inserted.

According to another aspect of the present invention, an oxygen concentration sensor includes a sensor element having an atmospheric chamber therein, a heater inserted in the atmospheric chamber, and a holder for holding the heater in the atmospheric chamber. The holder includes a cylindrical portion for covering an outer periphery of the heater and a plurality of cantilever elastic pieces provided at a lower portion of the cylindrical member.

The plurality of cantilever elastic pieces includes at least two heater supporting portions for elastically contacting with the outer periphery of the heater and at least two electrode connecting portions for elastically contact with the inner electrode.

As the structure of the cantilever elastic pieces is simple, because each of the cantilever elastic pieces includes only either the heater supporting portion or the electrode connecting portion. Accordingly, it is easy to manufacture the holder. In addition, it is preferable that the cantilever elastic pieces having the heater supporting portion is alternately arranged with the elastic pieces having the electrode connecting portion so that the heater can be supported in good balance.

According to further another aspect of the present invention, an oxygen concentration sensor includes a sensor element having an atmospheric chamber therein, a heater inserted in the atmospheric chamber, a holder for holding the heater in the atmospheric chamber. The holder includes a holding portion for holding the heater. The holding portion includes a heater supporting portion formed on an inside thereof for elastically supporting the heater and an electrode connecting portion formed on an outside thereof for elastically contacting with an inner electrode.

In this structure, as the holding portion of the holder includes the heater supporting portion and the electrode connecting portion, both of which have elasticy, the heater can be firmly supported and contact with the inner electrode.

According to still another aspect of the present invention, an oxygen concentration sensor includes an sensor element having an atmospheric chamber therein, a heater inserted in the atmospheric chamber, and a holder for holding the heater in the atmospheric chamber. The holder has elasticy, and an innermost diameter of the holder is smaller than a diameter of the heater, while the outermost diameter of the holder is larger than the inner diameter of the atmospheric chamber, in a natural condition.

In this structure, as the holder itself has elasticy and the heater and the atmospheric chamber have the above relationship in the size of the diameters, it is easy to hold the heater in the sensor element and to connect with the inner electrode certainly.

According to a oxygen concentration sensor of the present invention, the heater is fixed to the sensor element by the holder having a plurality of cantilever elastic pieces.

For this reason, even if the elastic pieces in the holder are largely displaced, allowable limit of the sensor element for dispersion of the heater and the sensor element in size and shape due to manufacturing errors can be enlarged, because the variation in the elastic force applied to the heater or the inner electrode is small. Therefore, it is possible to improve the reliability.

In addition, a contacting area between the holder and the sensor element is small, it is easy to assemble the holder into the sensor element.

If an external shock or vibration is applied to the oxygen concentration sensor, the heater supporting portion, the electrode connecting portion and the like are elastically deformed so as to absorb these shock and vibration. For this reason, the holder can hold the heater in the atmospheric chamber without causing any damage to the heater and the inner electrode.

As described above, according to the present invention, it is possible to provide an oxygen concentration sensor with a simple assembly of the heater into the sensor element and without damage to the heater.

Other objects and features of the invention will appear in the course of the description thereof, which follows.

BRIEF DESCRIPTION OF THE DRAWINGS

Additional objects and advantages of the present invention will be more readily apparent from the following detailed description of preferred embodiments thereof when taken together with the accompanying drawings in which.

DETAILED DESCRIPTION OF THE PREFERRED EMBODIMENTS

The preferred embodiments of the present invention are described with reference to the accompanying drawings.

An oxygen concentration sensor according to a first embodiment of the present invention is described with reference to FIGS. 1 through 8.

Figure 1:
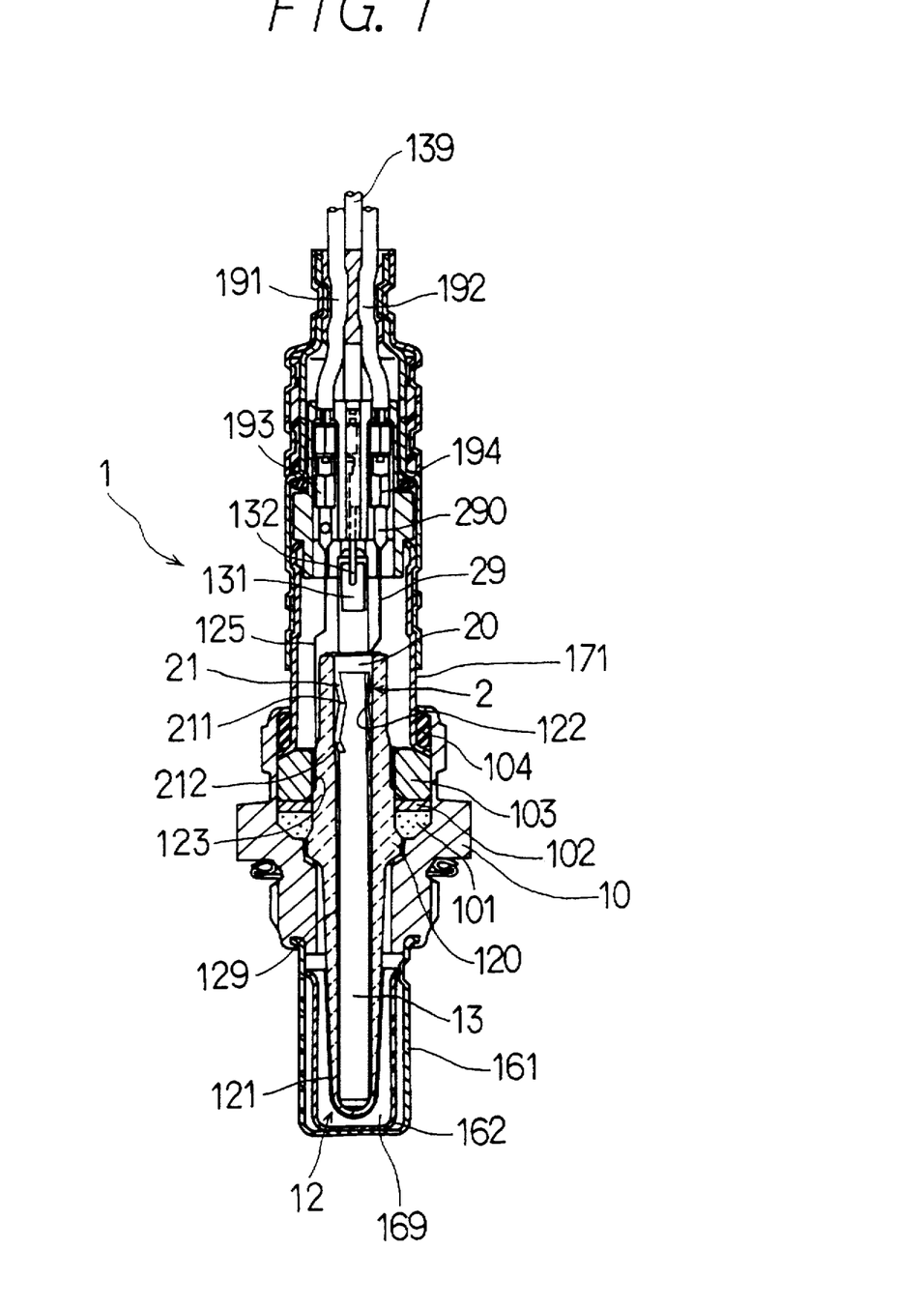
FIG. 1 is a cross-sectional explanatory view of an oxygen concentration sensor according to a first embodiment.

As shown in FIG. 1, an oxygen concentration sensor 1 of the first embodiment includes a sensor element 12 having an atmospheric chamber 129 therein and a heater 13 inserted into the atmospheric chamber with a holder 2.

As shown in FIGS. 2 through 5, holder 2 includes a cylindrical portion 20 for covering an outer periphery of heater 13, and three cantilever elastic pieces 21 provided at a lower end portion of cylindrical portion 20. Elastic pieces 21 include a heater supporting member 211 elastically contacting with the outer periphery of heater 13, and an electrode connecting portion 212 elastically contacting with an inner electrode 122 disposed in atmospheric chamber 129.

As shown in FIG. 1, oxygen concentration sensor 1 has sensor element 12 inserted into a housing 10.

Housing 10 includes a crimped portion at an upper end. By crimping the crimped portion, sensor element 13 is fixed to housing 10 with a ring packing 104, a cover 171, an insulator 103, a packing 102 and a talc 101 therebetween.

At a lower side of housing 10, measured gas side covers 161 and 162 having a double structure are provided to form a measured gas chamber 169.

Sensor element 12 includes a cup-shaped solid electrolyte 120 made of zirconia to form an atmospheric chamber 129 therein. Outer electrode 121 made of platinum layer is provided outside of solid electrolyte 120, while inner electrode 122 made of platinum layer is provided on an inner surface of solid electrolyte facing atmospheric chamber 129.

At outer electrode 121 is disposed an electrode terminal 123 of thin heat-resistant spring steel for taking out the output. A lead wire 125 extending from electrode terminal 123 is connected to a terminal 193 provided at an another lead wire 191.

In addition, inner electrode 122 is electrically conducted to a lead portion 29 of a later-described holder 2 via elastic pieces 21. A terminal 290 formed at lead portion 29 is connected to a terminal 194, for receiving terminal 290, provided at lead wire 192. The holder 2 is also made of thin heat-resistant spring steel.

Heater 13, inserted into the above-mentioned sensor element 12, includes a ceramic supporter and a heating element incorporated into the ceramic supporter. The heating element is electrically conducted to an electrode 131 provided at an upper portion of heater 13. Electrode 131 is connected to an outside power source via lead wires 132 and 139.

Next, the above-described holder 2 according to the first embodiment is described.

As shown in FIGS. 2 through 6, holder 2 includes a cylindrical portion 20, a flange portion 201 and a lead portion 29 at an upper end of cylindrical portion 20, and an electrode connecting portion 212 at a lower end of cylindrical portion 20. Elastic piece 21 includes a heater holding portion 211 at a middle portion and an electrode connecting portion 212 at a lower end.

Figure 7:
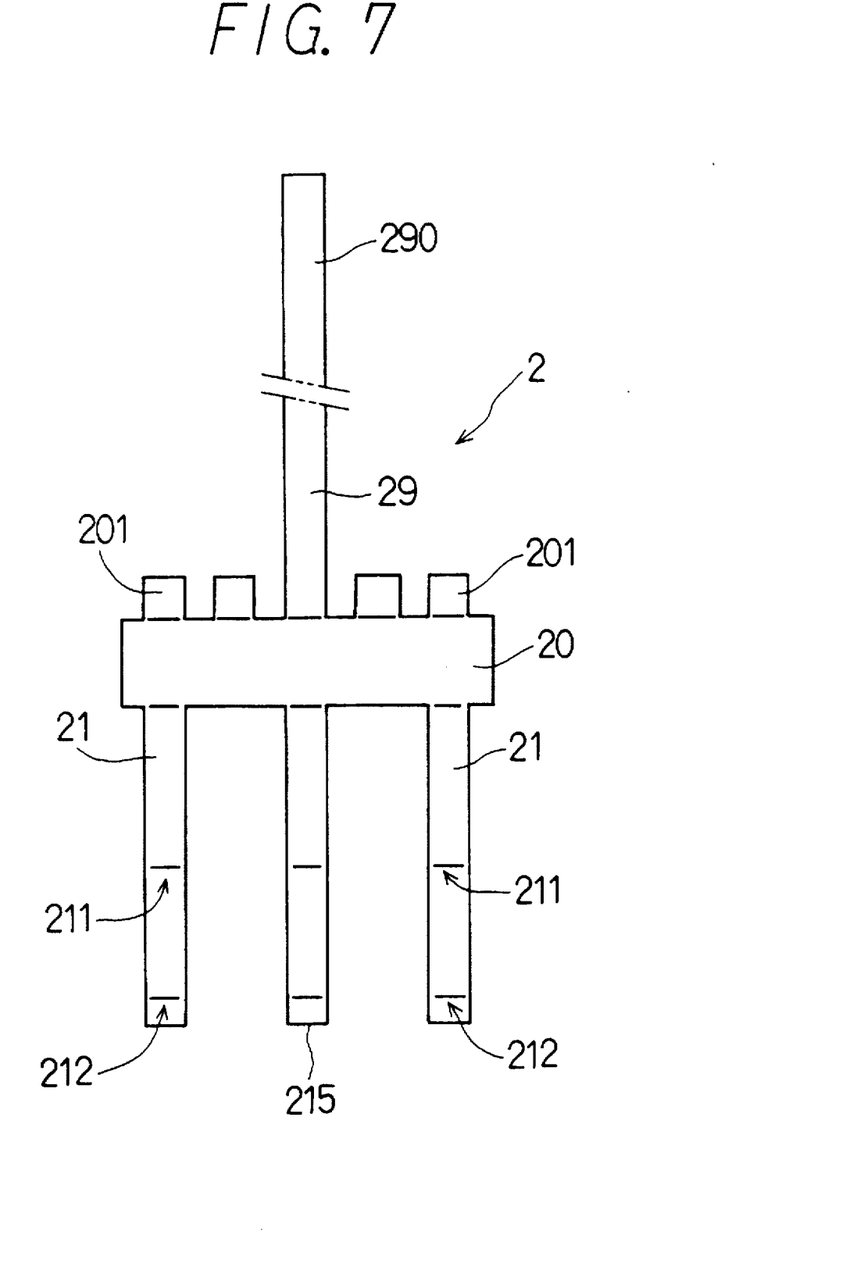
FIG. 7 is a plan development view illustrating the holder according to the first embodiment.
Figure 8:
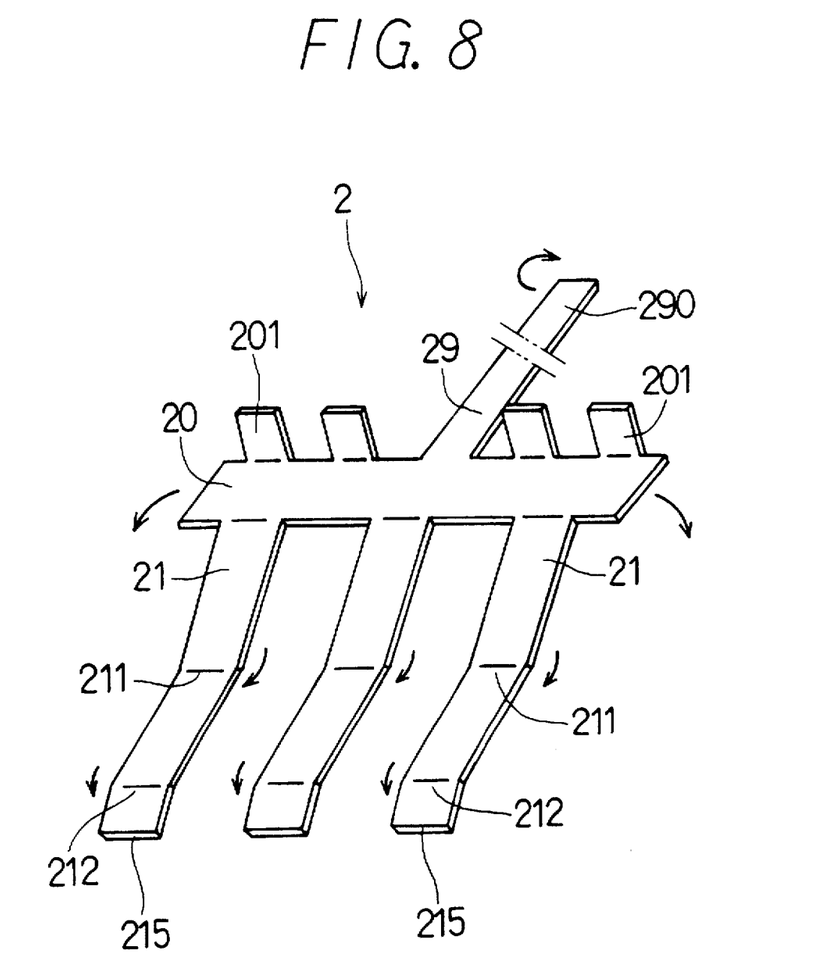
FIG. 8 is a perspective development view illustrating the holder according to the first embodiment.

Holder 2 is formed by punching a heat-resistant spring steel into a shape shown in FIG. 7 and bending the spring steel along arrows illustrated in FIG. 8.

Cylinder portion 20 is formed in a tubular shape so as to include heater holding portion 211 and electrode connecting portion 212. Heater holding portion 211 is formed by bending middle portions and tips 215 of elastic pieces 21 radially inwardly of cylindrical portion 20, and electrode connecting portion 212 is formed by bending a lower portion between the middle portions and tips 215 radially outwardly of cylindrical portion 20.

Figure 5:
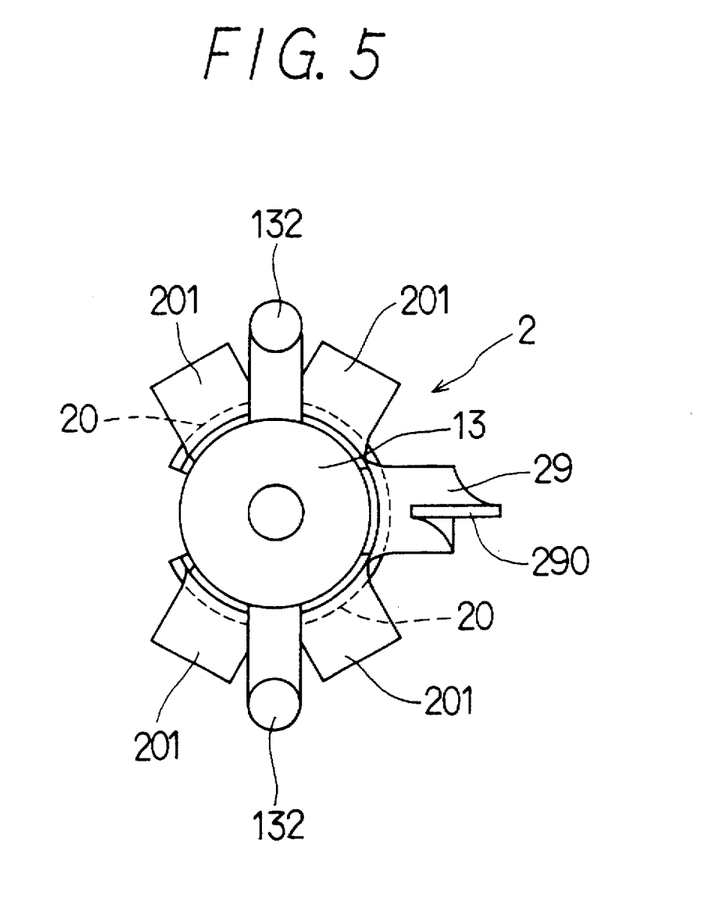
FIG. 5 is a plan view illustrating the assembly of the holder and the heater according to the first embodiment.
Figure 6:
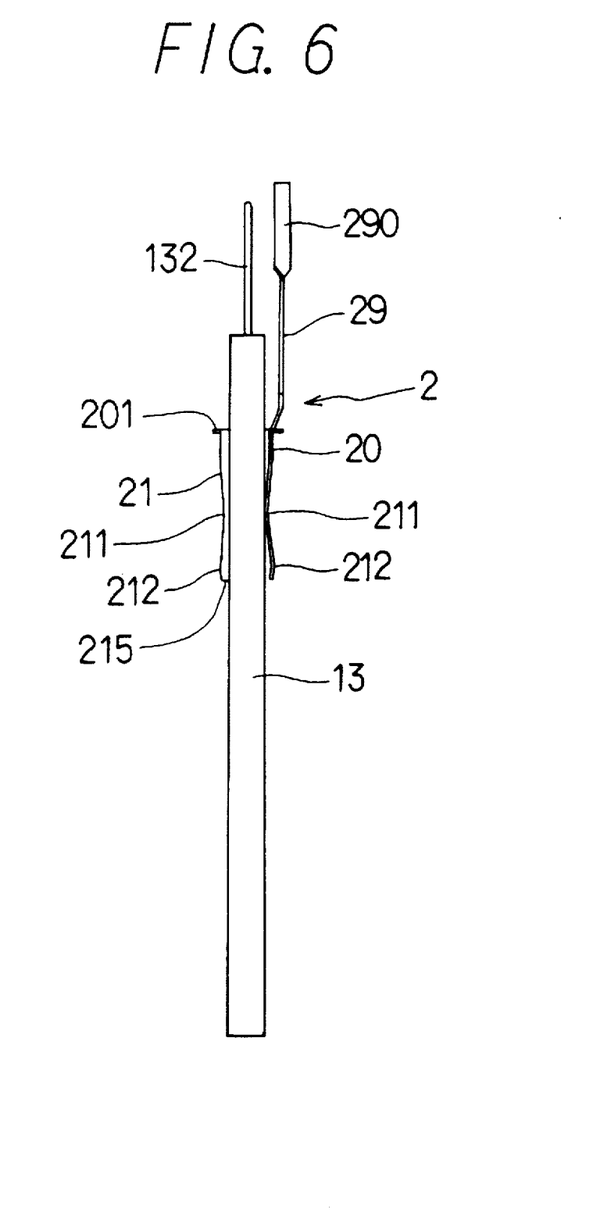
FIG. 6 is a cross-sectional view illustrating the assembly of the holder and the heater according to the first embodiment.

FIG. 5 shows that the cylinder portion 20 has first and second free side edges disposed in opposed, facing relation and having a gap therebetween at approximately the eight and ten o'clock positions in the Figure.

When heater supporting portion 211 and electrode connecting portion 212 are bent, the maximum size of the diameter between each of tip end portions of elastic pieces 21 should be smaller than the diameter of atmospheric chamber 129.

Figure 2:
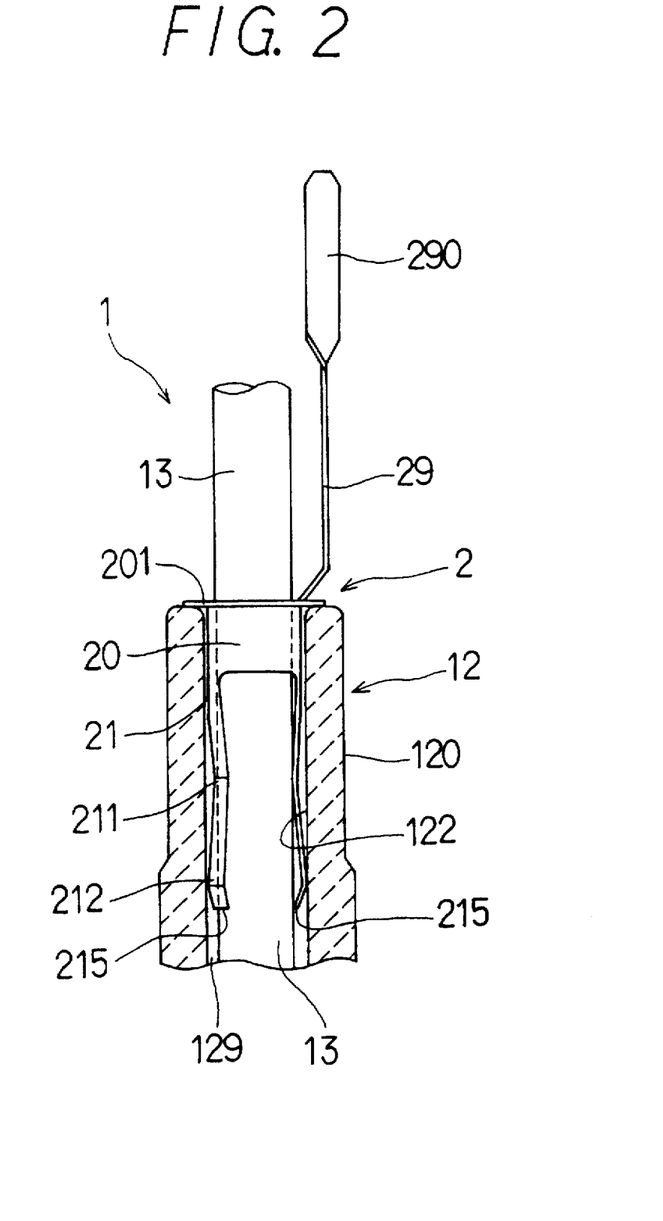
FIG. 2 is an enlarged explanatory view of the main portion the oxygen concentration sensor according to the first embodiment.
Figure 3:
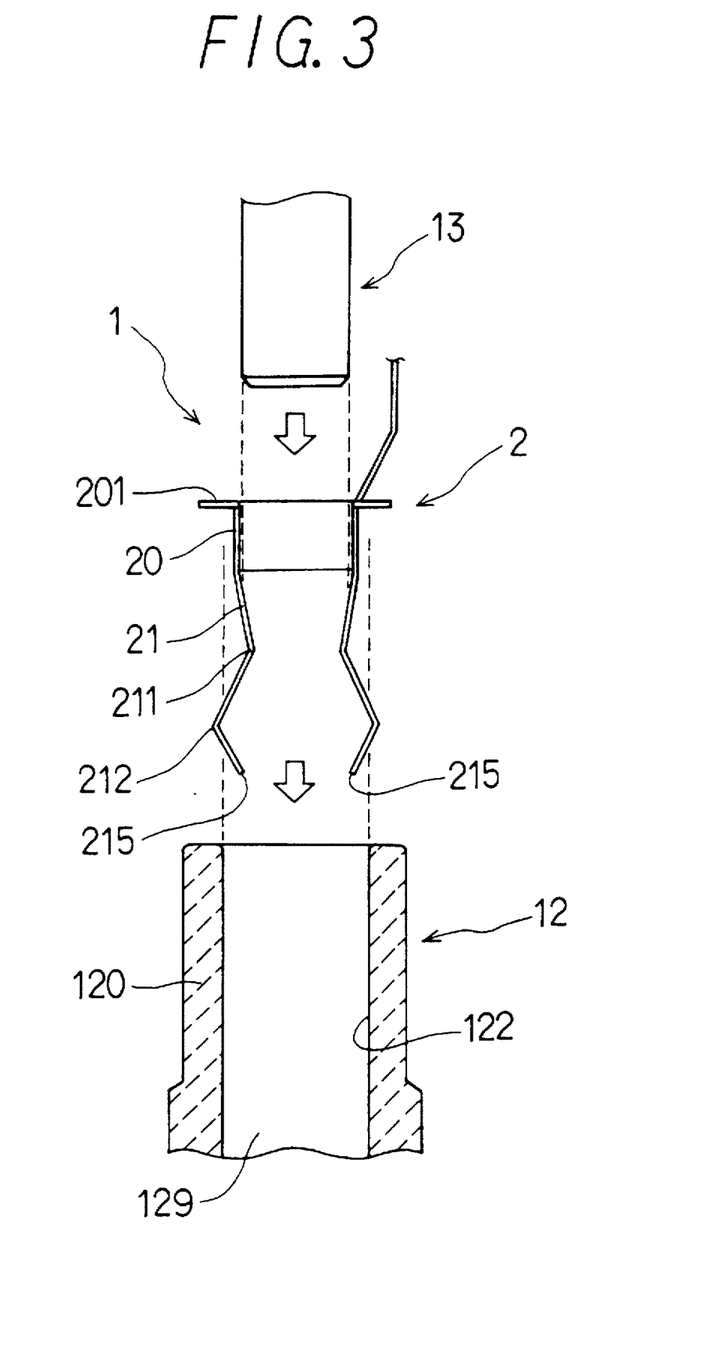
FIG. 3 is a development explanatory view of the oxygen concentration sensor according to the first embodiment.
Figure 4:
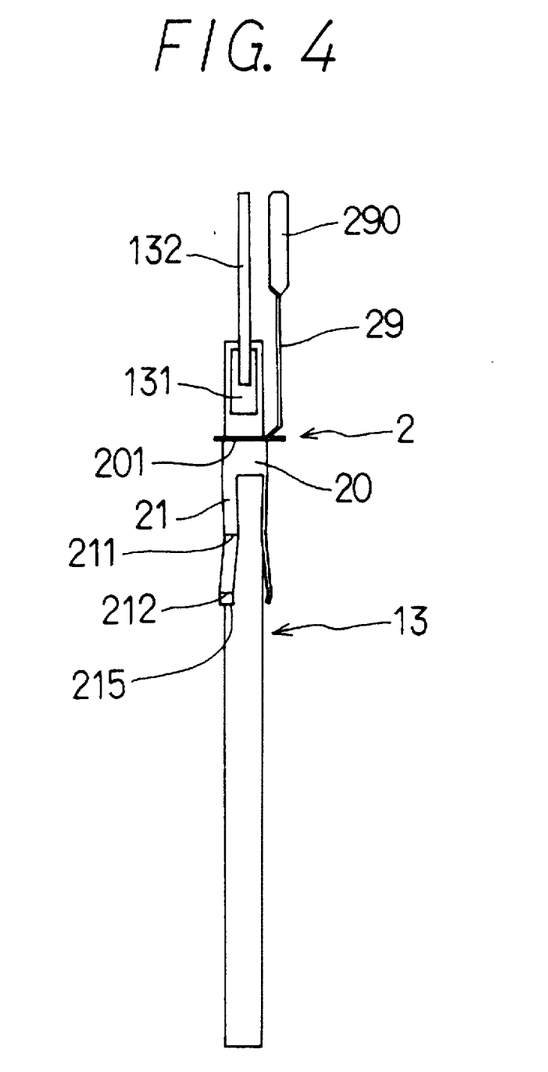
FIG. 4 is an explanatory view illustrating the assembly of a holder and a heater according to the first embodiment.

Flange portion 201 is bent radially outside, and terminal 290 is formed by twisting an upper portion of lead portion 29 vertically (shown in FIGS. 2 and 5).

Next, an operation and effect according to the first embodiment is described.

When heater 13 is assembled into sensor element 12 with holder 2, holder 2 is first inserted into an inside of atmospheric chamber 129 and fixed to an upper portion of sensor element 12 by flange portion 201 bent externally in the radial direction. At this time, the minimum diameter between each of elastic pieces is smaller than the outer diameter of heater 13.

Then, heater 13 is inserted into holder 2. Therefore, heater supporting portion 211 in holder 2 is externally pressed in the radial direction and electrode contacting portion 212 is in contact with inner electrode 122.

Elastic pieces 21 are band-like members extending downward from cylindrical portion 20. The upper end portion is a fixed end fixed to the cylinder portion, and the lower end portion is a free end. Other parts of these elastic pieces 21 except heater supporting portion 211 and electrode connecting portion 212 make no contact with heater 13 and inner electrode 122.

For this reason, as heater 13 is cantilever-fixed by means of heater supporting portion 211 and electrode connecting portion 212, in case that any shocks or vibrations are externally applied to the heater of oxygen concentration sensor, these shocks or vibrations are alleviated by the elastic deformation of elastic pieces 21. Therefore, inner electrode 122 and heater 13 are prevented from being damaged.

As heater 13 is fixedly pressed with elastic force given by the above-mentioned cantilever elastic pieces 21, the variation in pressing force is small even when the elastic pieces are largely displaced. As a result, allowable limit of the sensor element for dispersion of the heater and the sensor element in size and shape due to manufacturing errors can be enlarged, thus improving the reliability.

In addition, as a contacting area between holder 2 and sensor element 12 is small and the maximum diameter between each of tip end portions of elastic pieces 21 is smaller than the diameter of atmospheric chamber 129, it is easy to assemble holder 2 into sensor element 12.

Cylindrical portion 20 of the above-mentioned holder 2 includes flange portion 201 at an upper portion. Holder 2 is engaged with the upper portion of sensor element 12 by flange portion 201, thereby preventing holder 2 from falling into atmospheric chamber 129.

As holder 2 can take out the output of inner electrode 122 via lead portion 29, holder 2 can function as a lead wire, which is separately provided on the holder in the conventional oxygen concentration sensor, for taking out the output of inner electrode 122, thereby reducing the number of component parts. In addition, since elastic pieces 21 can be elastically deformed, the output of the inner electrode can be certainly taken out without any adverse influence by vibration, heat or the like.

Furthermore, holder 2 can be manufactured by simple process and method such as a method for punching a metal plate into a desired shape and sequentially bending the metal plate.

Therefore, according to this embodiment, it is possible to provide an oxygen concentration sensor capable of easily assembling a heater into a sensor element without any damage of the heater.

Next, a second embodiment of the present invention will be described.

Figure 9:
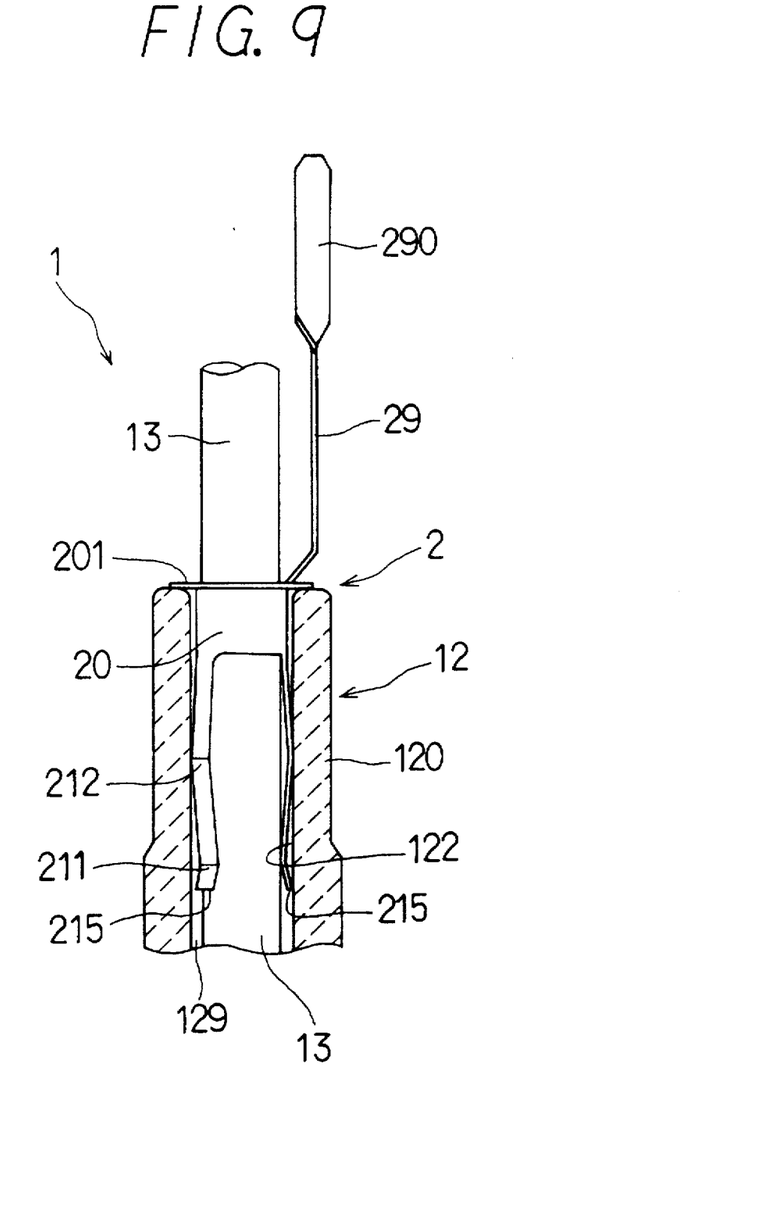
FIG. 9 is an enlarged explanatory view of the main portion of an oxygen concentration sensor according to a second embodiment.
Figure 10:
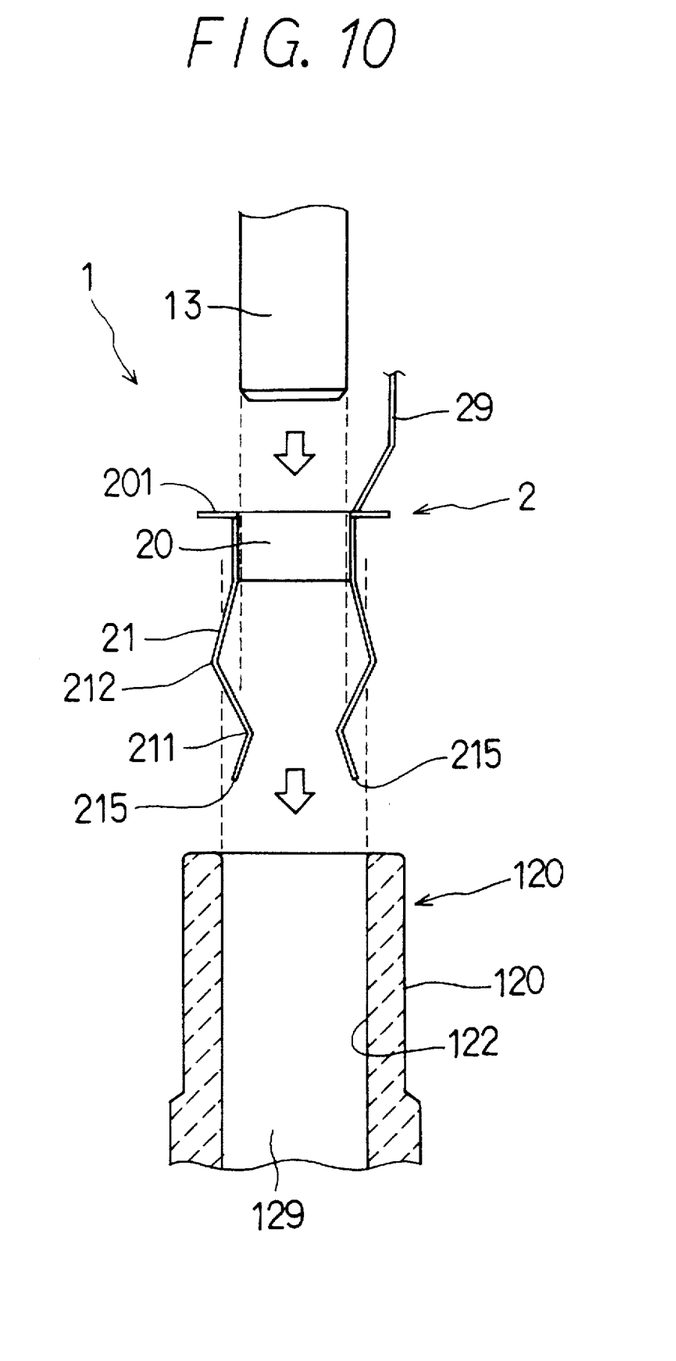
FIG. 10 is a development explanatory view of the main portion of the oxygen concentration sensor according to the second embodiment.

In the second embodiment, an oxygen concentration sensor includes an electrode connecting portion 212 in a middle part of elastic pieces 21 of a holder 2, and a heater supporting portion 211 at a lower end of the elastic pieces as shown in FIGS. 9 and 10.

Holder 2 is formed by punching a heat-resistant spring metal into a shape same as the first embodiment shown in FIG. 7 and bending the metal into the shape as illustrated in FIG. 10. That is to say, a cylinder portion 20 is formed in a tubular shape, and elastic pieces 21 is bent in a way that the lower end between the middle and a tip 215 of is bent radially inside of cylinder portion 20 and that the middle portion and tip 215 of elastic pieces 21 are bent radially outside of cylinder portion 20, thereby forming heater supporting member 211 and electrode connecting portion 212.

In the present embodiment, same reference numerals are given to components which have same or equivalent functions as in the first embodiment.

Additionally, a terminal 290 for connecting a terminal 194 therewith is formed by twisting an upper portion of the lead wire 29 vertically.

When heater 13 is assembled into sensor element 12 with the above-mentioned holder 2, only heater supporting member 211 of elastic pieces 21 makes contact with heater 13 and inner wall of cylindrical portion 20 makes no contact with heater 13 as shown in FIGS. 9 and 10.

Then, holder 2 assembled in heater 13 is inserted into atmospheric chamber 129 of sensor element 12 so that claw portion 201 is fixed to the upper portion of sensor element 12.

The other features are same as in the first embodiment.

According to oxygen concentration sensor 1 of the present embodiment, since the distance where electrode connecting portion 212 makes contact with inner electrode 122 of sensor element 12 is short, it is easy to assemble holder 2 into sensor element 12, and inner electrode 122 is not damaged. Moreover, the possibility of destruction of sensor element 12 is lowered.

The other operation and effect are same as in the first embodiment.

A third embodiment of the present invention will now be described.

Figure 11:
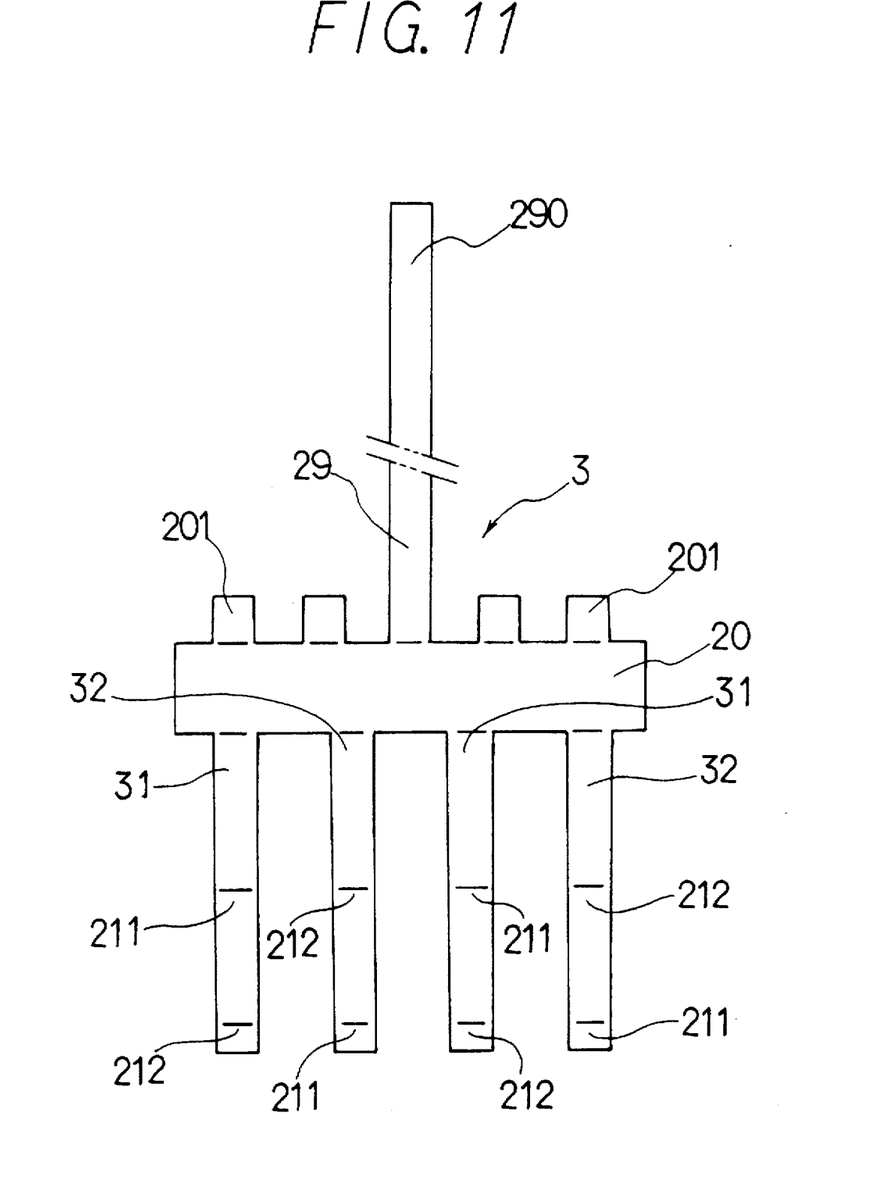
FIG. 11 is a plan development view illustrating a holder according to a third embodiment.
Figure 12:
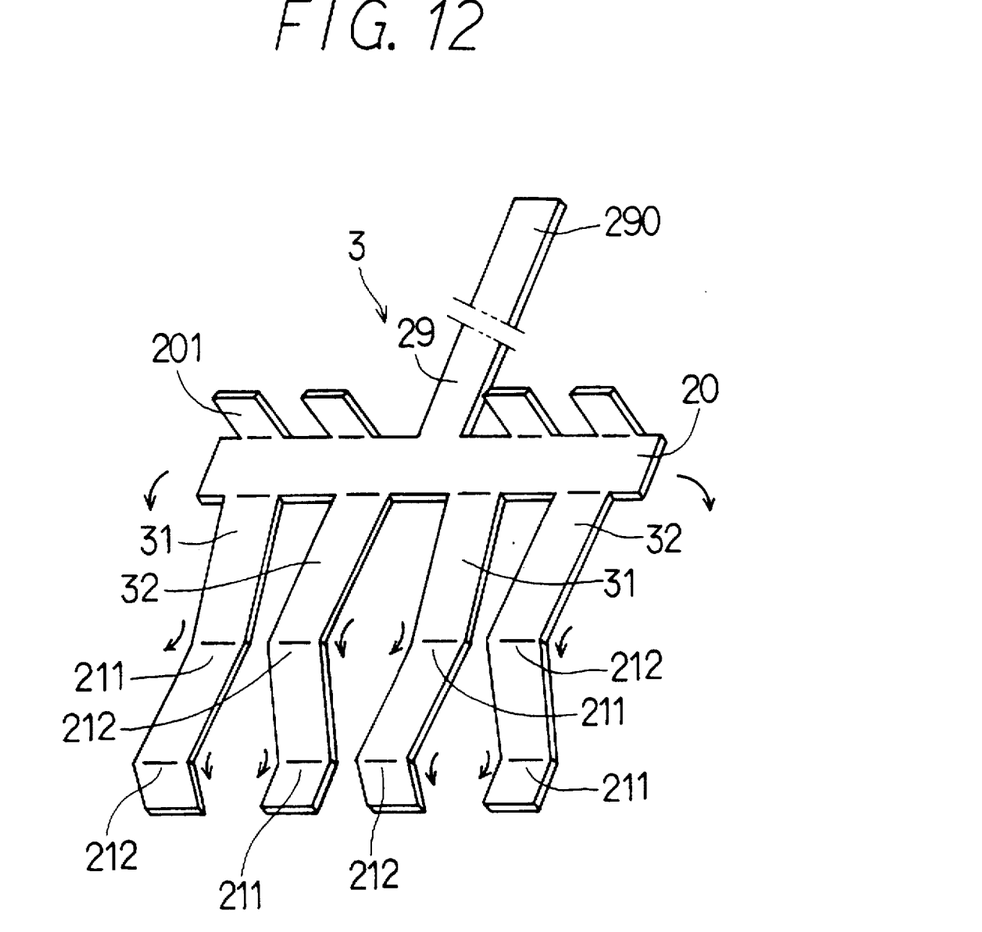
FIG. 12 is a perspective development view illustrating the holder according to the third embodiment.

As shown in FIGS. 11 and 12, in the third embodiment, an oxygen concentration sensor has four of two kinds of elastic pieces 31 and 32 provided at a holder 3 alternately. First elastic pieces 31 are bent along an arrow as illustrated in FIG. 12, to form a heater supporting portion 211 in a middle portion and an electrode connecting portion 212 provided at a lower end portion of the elastic piece. On the contrary, second elastic pieces 32 adjacent to first elastic pieces 31 includes electrode connecting portion 212 in the middle and heater supporting portion 211 at the lower end portion of the elastic pieces.

That is, when holder 3 is formed in a tubular configuration, heater supporting portion 211 and electrode connecting portion 212 are alternately provided at the middle and the lower end portion of first elastic pieces 31.

The other features are same as in the first embodiment.

According to oxygen concentration sensor of the third embodiment, since holder 3 is pressed by heater supporting portions 211 at different positions in a longitudinal direction of heater 13, heater 13 is firmly supported in sensor element 12. Additionally, since pressing force by heater supporting portions 211 is not applied to one identical circumference of heater 13, but the force is dispersed, heater 13 being thereby less damaged.

The other operation and effect are same as in the first embodiment.

Next, a fourth embodiment of the present invention will be described.

Figure 13:
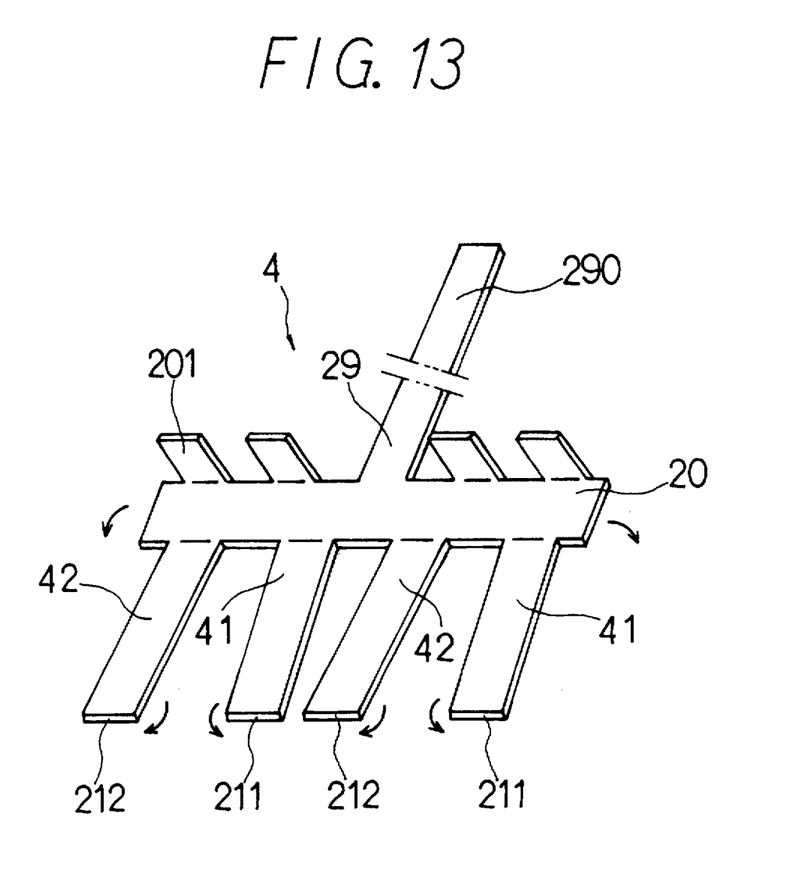
FIG. 13 is a perspective development view illustrating a holder according to a fourth embodiment.

As shown in FIG. 13, oxygen concentration sensor of the fourth embodiment has four of two kinds of elastic pieces 41 and 42 provided at a holder 4 alternately. Elastic pieces 41 are bent along an arrow as illustrated in FIG. 13 to form a heater supporting portion 211 provided in a lower end portion of the elastic piece. On the contrary, second elastic pieces 42 adjacent to first elastic pieces 41 includes electrode connecting portion 212 at the lower end portion of the elastic pieces.

The other features are same as in the first embodiment.

According to the fourth embodiment, in holder 4 of oxygen concentration sensor, first elastic pieces 41 includes only heater supporting portion 211 and second elastic pieces includes only electrode connecting portion 212 only; therefore, the structure is simple and it is easy to manufacture the holder.

The other operation and effect are same as in the first embodiment.

Further, holder 4 is assembled into solid electrolyte 120 while a tip end portion of heater 13 contacts with an inner surface of a tip end portion of cup-shaped solid electrolyte 120.

Even when the tip end portion of heater 13 contacts with the inner surface of the tip end portion of solid electrolyte 120, it is hard for a bending force or the like to be applied to heater 13, because heater 13 is supported in holder 4 at only one position in the axial direction.

Further, since the heating portion of heater 13 is close to the tip end portion of solid electrolyte 120, it is possible to improve the characteristics for increasing the temperature of solid electrolyte 120.

The present invention having been described should not be limited to the disclosed embodiments, but it may be modified in many other ways without departing from the scope and the spirit of the invention. Such changes and modifications are to be understood as being included with the scope of the present invention as defined by the appended claims.

What is claimed is:

1. An oxygen concentration sensor comprising:
   a cup-shaped solid electrolyte element having an open end at one end thereof and a closed end at the other end thereof, said solid electrolyte element forming an atmospheric chamber therein;
   a heater inserted in said atmospheric chamber;
   a holder for holding said heater in said atmospheric chamber, said holder including:
      a cylindrical portion having first and second free side edges disposed in opposed, facing relation and having a gap therebetween, said cylindrical portion having a diameter larger than a diameter of said heater and smaller than a diameter of an inner surface of said solid electrolyte,
      a plurality of elongated cantilever elements, each integrally provided with said cylindrical portion so as to extend longitudinally from an end of said cylindrical portion, each said cantilever element having a heater supporting portion for supporting said heater, said heater supporting portions of said plurality of cantilever elements elastically contacting said heater at plural, discrete positions about a circumference of said heater, each said cantilever element also having a fixing portion, said fixing portions of said plurality of cantilever elements elastically contacting an inner surface of said solid electrolyte element.

2. An oxygen concentration sensor according to claim 1, further comprising:
   an inner electrode provided on an inner surface of said solid electrolyte element; and
   an outer electrode provided on an outer surface of said solid electrolyte element;
   wherein said fixing portion further includes an electrode connecting portion for elastically contacting with said inner electrode.

3. An oxygen concentration sensor according to claim 2, wherein said holder includes a lead portion for taking out an output of said inner electrode.

4. An oxygen concentration sensor according to claim 1, wherein said holder is made from a heat-resistant spring metal plate by punching.

5. An oxygen concentration sensor according to claim 4, wherein said heater supporting portion is formed by bending said heat-resistant spring metal plate.

6. An oxygen concentration sensor according to claim 4, wherein said heater supporting portion contacts with said heater at least at two positions which are different from each other in a circumferential direction of said heater.

7. An oxygen concentration sensor according to claim 1, wherein an end portion of said holder has a diameter smaller than that of an inner surface of said solid electrolyte element.

8. An oxygen concentration sensor according to claim 1, wherein a tip end portion of said heater contacts with an inner surface of a tip end portion of said solid electrolyte element.

9. An oxygen concentration sensor comprising:
   a cup-shaped solid electrolyte element having an open end at one end thereof and a closed end at the other end thereof, said solid electrolyte element forming an atmospheric chamber therein;
   a heater inserted in said atmospheric chamber;
   a holder for holding said heater in said atmospheric chamber, said holder including:
      a cylindrical portion having first and second free side edges disposed at opposed facing relation and having a gap therebetween, said cylindrical portion having a diameter larger than that of said heater and smaller than that of said inner surface of said solid electrolyte;
      a flange portion integrally provided with one end of said cylindrical portion and projecting radially outwardly therefrom, said flange portion having an inner diameter larger than that of said heater and a surface of said flange contacting one end surface of said solid electrolytes; and
      an elastic piece integrally provided with and extending generally longitudinally from an other end of said cylindrical portion, said elastic piece including a heater supporting portion for elastically contacting with a surface of said heater and a fixing portion for elastically contacting with an inner surface of said solid electrolyte element.

10. An oxygen concentration sensor comprising:
    a sensor element having an atmospheric chamber therein;
    an inner electrode provided on an inner surface of said sensor element;
    an outer electrode provided on an outer surface of said sensor element;
    a heater inserted in said atmospheric chamber; and
    a holder for holding said heater in said atmospheric chamber, said holder including:
       a cylindrical portion for covering an outer periphery of said heater, said cylindrical portion having first and second free side edges disposed at opposed facing relation and having a gap therebetween, said cylindrical portion having a diameter larger than that of said heater and smaller than that of an inner surface of said sensor element; and
       a plurality of cantilever elastic pieces provided at and each extending longitudinally from an end portion of said cylindrical portion, each of said cantilever elastic pieces including:
          a single fixing portion for elastically contacting with said inner electrode, and
          a single supporting portion for elastically contacting with the heater.

11. An oxygen concentration sensor according to claim 10, wherein said holder is made from a heat-resistant spring metal plate by punching.

12. An oxygen concentration sensor according to claim 10, wherein said heater supporting portion is formed by bending said heat-resistant spring metal plate.

* * * * *